United States Patent [19]
Wang

[11] Patent Number: 5,756,705
[45] Date of Patent: May 26, 1998

[54] METHOD FOR LABELING OLIGONUCLEOTIDE WITH AMMONIA-SENSITIVE LIGANDS

[76] Inventor: Edge Renfeng Wang, 18886 Sydney Cir., Castro Valley, Calif. 94546

[21] Appl. No.: 811,712

[22] Filed: Mar. 5, 1997

[51] Int. Cl.[6] .............................. C07H 1/02; C07H 21/00; C07H 21/04
[52] U.S. Cl. ......................................... 536/25.32; 536/25.3
[58] Field of Search ............................... 536/25.3, 25.32

[56] References Cited

U.S. PATENT DOCUMENTS 4,965,349  10/1990  Woo et al. ............................ 536/25.32

Primary Examiner—Gary L. Kunz

[57] ABSTRACT

The invention provides method for labeling oligonucleotides and their analogs with ammonia-sensitive ligands. A non-ammonia cocktail is used for cleavage and deprotection in combination with base labile linkers. The labeling process is done on the solid phase and cleaved by the non-ammonia cocktail to prevent the ligand from decomposition.

14 Claims, No Drawings

METHOD FOR LABELING OLIGONUCLEOTIDE WITH AMMONIA-SENSITIVE LIGANDS

FIELD OF THE INVENTION

The field of the invention is reagents and methods for the synthesis of labeled polynucleotides.

BACKGROUND OF THE INVENTION

Non-radioisotopic labeling of oligonucleotides has found wide applications in nucleic acid analysis, such as DNA sequencing, mapping, DNA/RNA blotting, and fluorescence quenching assays. The ability to label an oligonucleotide with ligand at any selected position along the sequences (5' end, 3' end and the middle of the sequence) is particularly advantageous (World patent WO92/21266, WO95/02638). Currently, there are two ways to label a synthetic oligonucleotide. In the first method, the labeling is done post-synthesis in the liquid phase. An oligonucleotide can be first synthesized on, for example, a DNA synthesizer, then cleaved. During the synthesis, an amino group is incorporated into the potential position for labeling on the sequence of the oligonucleotide, either at the ends or in the middle. The oligonucleotide then reacts with an activated ester of the ligand in an organic solution. The solvent is then removed and the product is purified. This appproach has several drawbacks: 1) it involves many steps and is time-consuming; 2) It requires large access of the labeling reagent; 3) it requires steps to remove organic solvent; 4) the product has to be purified to remove the unreacted reactants and by-products, and 5) addtional purification sometimes is needed before the labeling reaction takes place. The second approach is solid phase synthesis on the syntheizer, for example, using ligand-phosphoramidite. This method is fast and the post-synthesis is simple. However, since the cleavage of the oligonucleotide is done with fairly strong bases, mostly concentrate ammonium hydroxide, some ligands, such as TAMRA and Texas red, are decomposed under such harsh conditions. Furthermore, it is difficult, very expensive and sometimes impossible to make phosphoramidite with some of the ligand.

The present invention comprises a method for post-synthesis labeling of oligonucleotides and their analogs. This method takes the advantages of solid phase synthesis without the necessary requirement of using phosphoramidite, which sometimes is unavailable for certain ligands. The novel cleavage cocktail used in this invention for cleaving the labeled oligonucleotide from the support conserves the ammonia-sensitive ligands from significant decomposition. Furthermore, the lower concentration of alcohol in the non-ammonia cleavage cocktail reduces the cost and environmental contamination and can be directly used in the following purification steps.

Relevant Literture

Relevant literature includes Nelson (1992) U.S. Pat. No. 5,141,813, Nelson et al. (1995) U.S. Pat. No. 5,451,463, and Nelson (1995) U.S. Pat. No. 5,401,837; Woo et al. (1990) U.S. Pat. No. 4,965,349 and; Woo et al. (1993) U.S. Pat. No. 5,231,191.

SUMMARY OF THE INVENTION

The current invention provides method for labeling oligonucleotides and their analog with ammonia-sensitive ligands such as some fluorescence dyes.

The general method for labeling an oligonucleotide and its analog with ammonia-sensitive ligands involves:

a) synthesizing an oligonucleotide sequence on a solid support with a base-labile linker;

b) introducing a reactive group at the desired position of the sequence;

c) coupling the ligand to the said reactive group;

d) cleaving the oligonucleotide from the support with the non-ammonia cocktail comprising up 4–20% (V/V) of low alkyl alcohol.

An important aspect of this invention is that the combination of the base labile linker and the non-ammonia cleavage/deprotection cocktail allows the cleavage and deprotection of the labeled oligonucleotide under mild conditions to prevent ammonia-sensitive ligands from decomposition. Another important aspect of the invention is the use of non-phosphoramidite ligand, such as an activated ester, in the post-synthesis labeling on the solid support. This approach takes the advantages of solid phase synthesis, such as high coupling efficiency, minimal usage of reagents, and simplicity in removal of unreacted reactants and by-products, without suffering from the high cost and difficulties in preparing a phosphoramidite. Yet another important aspect of this invention is the use of lower concentration of alcohol in the non-ammonia cleavage/deprotection cocktail. This lower concentration of alcohol reduces the cost in preparing and disposing the cocktail and reduces the environmental contanimation.

DETAILED DESCRIPTION OF SPECIFIC EMBODIMENTS

The subject methods require a base-labile linker on the solid support for the synthesis and a non-ammonia reagent cocktail for the cleavage and deprotection of oligonucleotide. In a preferred embodiment, the base-labile linker has a structure

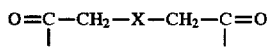

where X consists of a group comprising N, O, or S. In another preferred embodiment, the base-labile linker has a structure

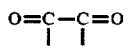

These base-labile structures make the cleavage faster and under mild non-ammonia conditions. For example, the cleavage can be done in concentrated ammonium hydroxide in less than 15 minutes or in the non-ammonia cocktail for less than one hour. Such mild cleavage conditions and less time not only make the process fast, but also reduce the possibility of producing impurities which sometimes are associated with ammonia cleavage under conventional conditions. The non-ammonia cleavage/deprotection cocktail contains a non-nucleophilic hindered alkylamine and a low alkyl alcohol in equeous solution. Generally, concentration of the low alkyl alcohol is about 4–20% (V/V). In a particular embodiment, the concentration of the low alkyl alcohol is about 10% (V/V). This lower concentration of the low alkyl alcohol not only reduces the cost in preparing and disposing the cocktail and reduces the environmental contanimation, but also makes it possible to load the labeled oligonucleotide into the cocktail directly to the purification cartridge, such as an OPC column. In a previous disclosure by Sam Woo, et al., (U.S. Pat. No. 5,231,191) higher concentration of the alcohol was used (20–33%). Such a solution with high concentration of alcohol can not be used as loading buffer for the cartridge purification because the oligonucleotide can not be retained in the cartridge in high organic content solution. Additional steps, such as dilution and evaporation, are needed in order to load the oligonucleotide to the purification cartridge. These steps increase the cost and time needed for the preparation of the oligonucleotide. With the current invention, there is no need to change the buffer system before loading the oligonucleotide to the purification cartridge because the lower alcohol concentration allows the retention of the labeled oligonucleotide. Although not necessary, it is desirable to keep the molar concentration of the non-nucleophilic hindered alkylamine same or similar to the concentration of the low alkyl alcohol. The cocktail functions even when the molar concentrations of the non-nucleophilic hindered alkylamine and the low alkyl alcohol are far apart. In one preferred embodiment, the concentration of the non-nucleophilic hindered alkylamine is 5–40% (V/V).The aqueous solution might also contain other components such as other organic and inorganic species. Preferably, the non-nucleophilic hindered alkylamine is selected from the group consisting of isopropylamine, t-butylamine, diethylamine, piperidine, t-amylamine, diisopropylamine and dipropylamine, and the low alkyl alcohol is selected from group consisting of methanol, ethanol and propanol. More preferably, the non-nucleophilic hindered alkylamine is t-butylamine and the low alkyl alcohol is methanol. Most preferably, the cocktail contains about 10% (V/V) of methanol and about 25% (V/V) t-butylamine.

The reactive group is selected from a group consisting of amine, thiol, aldehyde, hydroxyl, and halogen-containing groups. In one example, the reactive group is the 5'-hydroxyl group at the 5' end of the oligonucleotide. The ligands are in forms such as activated ester, hydrazide, halogenate, phosphoramidite. The reactive groups may be protected with protection groups such as DMT, MMT, LEV, Fmoc, TFA. The removal of the protection groups is done by treating the oligonucleotide on the solid support with a deprotection agent such as an acid or base. For example, in the case of Fmoc protection, the deprotection can be done with piperidine. If the reactive group is protected by DMT, MMT, or LEV, the deprotection can be done by treating the oligonucleotide with weak acids such as TCA, which is routinely used in the solid phase synthesis as a deblocking agent. All of these treatments for deprotection do not remove the oligonucleotide from the solid support. Following coupling of the ligand to the reactive group, the oligonucleotide is cleaved from the solid support by treating the support with the non-ammonia cocktail. The deprotection of the side chain can be done by leaving the oligonucleotide in the same cocktail at 50°–95° C. In some cases, the steps of cleavage and deprotection are combined.

EXAMPLES

1) A 15 mer of homo-T oligonucleotide is synthesized on a DNA synthesizer using the T-CPC containing the base-labile linker. At position 16 from 3' end, an MMT-protected amino linker is incorporated. The MMT group is then removed by deliver the delocking agent, TCA, to the column for about 5–7 minutes. The column is then washed with acetonitrile and dried with flowing gas. The column is then removed from the synthesizer. One syringe containing 0.5 ml of TAMRA-NHS/DMF solution (5 mg/ml) in the presence of triethylamine is connected to one end of the column and an empty syringe is connected at the other end of the column. The solution is pushed through the column back and forth every hour for eight hours. The column is then washed with DMF and acetonitrile three times each. One ml of the non-ammonia cocktail (10% methanol; 25% t-butylamine; 65% water) is pushed through the column in the same fashion every 10 minutes for one hour. The cocktail is then collected and sealed in a container. The cocktail is heated with 65° C. for 5 hours and removed under vacuum leaving the labeled oligonucleotide in the dry form.

2) A 15 mer homo-T oligonucleotide is synthesized on a DNA synthesizer using the T-CPC containing the base-labile linker. At position 10 from 3' end, a linker arm nucleotide (LAN)-T is incorporated, where the amino group is protected by Fmoc. At the end of the synthesis, the column is removed from the syntheizer and the CPG is removed from the column and collected in a reaction vessel. The CPG is then treated with 20% piperidine/DMF to remove Fmoc and then washed with DMF and acetonitrile three times each. The CPG is then added with 0.5 ml of DNP-X-NHS/DMF solution (5 mg/ml) in the presence of triethylamine and shaked overnight. The resin is then washed and dried under vacuum. One ml of the non-ammonia cocktail is added to the resin and incubated at 65° C. for 5 hours. The cocktail is then separated from the resin and dried under vacuum, leaving the labeled oligonucleotide in the dry form.

What is claimed is:

1. A method for labeling a synthetic oligonucleotide or its analog with ammonia sensitive ligands, said method comprising the steps of a) synthesizing the oligonucleotide sequence on a base-labile support, b) introducing a reactive group to the sequence, c) coupling the ligand to the reactive group; and cleaving said oligonucleotide from the support with a non-ammonia cocktail, wherein the improvement is said non-ammonia cocktail comprising water, a hindered alkylamine, and a maximum concentration of 4% to about 10% (v/v) of a lower alkyl alcohol.

2. A method according to claim 1 wherein said base labile support comprises a linker with the structure shown below:

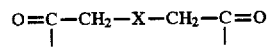

where X is N, O, or S.

3. A method according to claim 1 wherein said base labile support comprises a linker with the structure shown below:

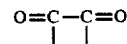

4. A method according to claim 1 wherein the concentration of said lower alkyl alcohol is about 10% (v/v).

5. A method according to claim 4 wherein the concentration of said non-nucleophilic hindered alkylamine is 5–40% (v/v).

6. A method according to claim 1 wherein said lower alkyl alcohol is selected from the group consisting of methanol, ethanol, and propanol.

7. A method according to claim 1 wherein said non-nucleophilic hindered alkylamine is selected from the group consisting of isopropylamine, t-butylamine, diethylamine, piperidine, t-amylamine, diisopropylamine, and dipropylamine.

8. A method according to claim 1 wherein said low alkyl alcohol is methanol.

9. A method according to claim 5 wherein said non-nucleophilic hindered alkylamine is t-butylamine.

10. A method according to claim 1 wherein said non-ammonia cocktail comprises about 10% (v/v) of methanol and 25% (v/v) of t-butylamine.

11. A method according to claim 1 wherein said ammonia-sensitive ligand comprises rhodamine or its derivatives.

12. A method according to claim 1 wherein said ammonia-sensitive ligand comprises Texas red or its derivatives.

13. A method according to claim 1 wherein said ammonia-sensitive ligand is acridine or its derivatives.

14. A method according to claim 1 wherein said ammonia-sensitive ligand is a nitro-containing dye.

* * * * *